(12) United States Patent
Distler et al.

(10) Patent No.: US 7,374,338 B2
(45) Date of Patent: May 20, 2008

(54) GANTRY FOR A COMPUTED TOMOGRAPHY APPARATUS AND METHOD FOR COOLING A GANTRY

(75) Inventors: Friedrich Distler, Fürth (DE); Rita Krug, Fürth (DE); Hans-Jürgen Müller, Pretzfeld (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/514,708

(22) Filed: Aug. 31, 2006

(65) Prior Publication Data

US 2007/0053500 A1 Mar. 8, 2007

(30) Foreign Application Priority Data

Aug. 31, 2005 (DE) .................. 10 2005 041 542

(51) Int. Cl.
*H01J 35/10* (2006.01)
(52) U.S. Cl. .......................................... 378/199; 378/4
(58) Field of Classification Search .................. 378/4, 378/199–200, 141
See application file for complete search history.

(56) References Cited

U.S. PATENT DOCUMENTS 6,289,073 B1* 9/2001 Sasaki et al. ................. 378/4
2004/0202287 A1* 10/2004 Muller ....................... 378/199

FOREIGN PATENT DOCUMENTS

DE 103 12 253 A1 10/2004

* cited by examiner

*Primary Examiner*—Hoon Song
(74) *Attorney, Agent, or Firm*—Schiff Hardin LLP

(57) ABSTRACT

A gantry for a computed tomography apparatus has a rotary carriage that is rotatable around an axis and a support ring arranged around the rotary carriage with a circumferential cooling channel. The support ring has a number of openings distributed around its circumference and forming a non-uniform opening pattern. The rotary carriage likewise has inflow and outflow openings that, in operation, overlap the openings on the stationary part of the computed tomography apparatus such that a coolant flows through between the support ring and the rotary carriage. A steady pressure fluctuation that leads to a reduction of the noise stress in operation ensues thanks to the non-uniform opening pattern.

15 Claims, 4 Drawing Sheets

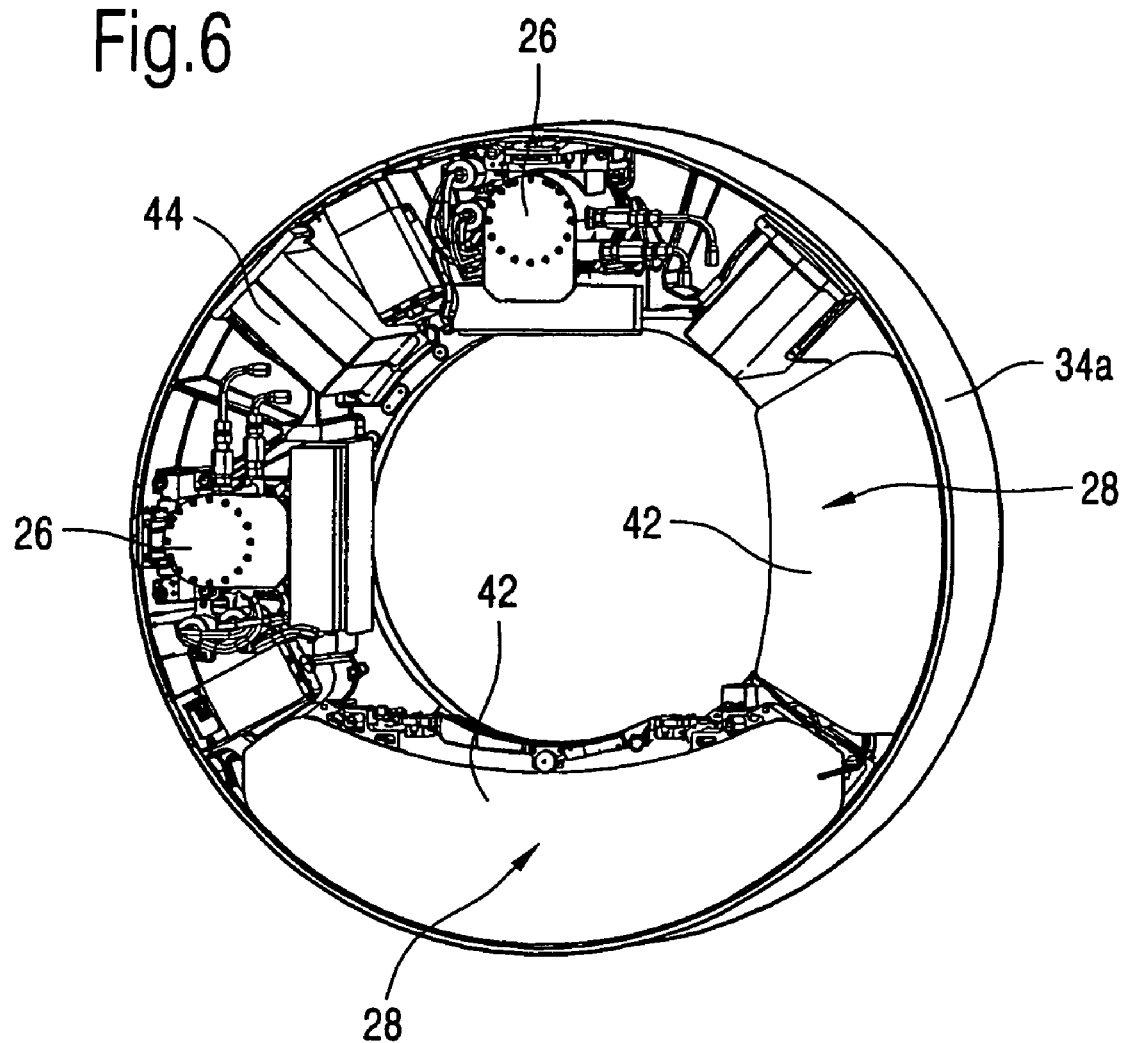

GANTRY FOR A COMPUTED TOMOGRAPHY APPARATUS AND METHOD FOR COOLING A GANTRY

BACKGROUND OF THE INVENTION

1. Field of the Invention

The present invention concerns a gantry for a computed tomography apparatus of the type having a rotary carriage that is rotatable around an axis and a support ring arranged around the rotary carriage with a circumferential cooling channel. The invention furthermore concerns a computer tomograph having such a gantry and a method for cooling such a gantry.

2. Description of the Prior Art

In a computed tomography apparatus three-dimensional slice images of the inside of a patient are generated by x-ray imaging method. For this purpose, two-dimensional x-ray slice images, from which a three-dimensional slice image is reconstructed, are generated by a scanning unit that normally includes an x-ray radiator rotating around the acquisition subject and an image acquisition system. The computed tomography apparatus typically has a stationary part that with a support ring is arranged around a patient acquisition space and a supporting body for the support ring. A rotatable rotary carriage that carries the x-ray radiator and an oppositely-situated x-ray detector is supported on the support ring. The combination of the rotary carriage together with the support ring is typically called a gantry.

A problem in such a computed tomography apparatus is the dissipation of the heat that accumulates in the x-ray radiator and the x-ray detector, because 99% of the energy used to generate an x-ray is converted into heat. Local air cooling, for example by means of a ventilator, cannot be used or can be used only in a limited manner in a computed tomography apparatus. The supply and discharge of a gaseous or liquid coolant by means of rigid or flexible coolant lines cannot be accomplished or can be accomplished only in a complicated manner, because of the necessity of not impairing the rotational capability of the gantry.

The cooling systems conventionally used in such computed tomography apparatuses generally include a number of heat exchangers that are installed inside the support ring. In order to efficiently dissipate heat accumulating at the rotating x-ray radiator from the inside of the rotary carriage, a heat exchanger that rotates with the rotary carriage is conventionally mounted in the immediate proximity of the x-ray radiator. This heat exchanger emits heat to the surrounding air. The heated air can be cooled, for example, by a second heat exchanger that dissipates the heat acquired from the air to a cooling system outside of the support ring.

An alternative concept for a cooling system is described in DE 103 12 253 A1, in which the components arranged in the gantry are cooled by compressed coolant air. The compressed coolant air flows via a nozzle ring into a rotatable rotary carriage, the nozzle ring having exhaust openings directed radially outwardly along its entire circumference. The heated air arrives via flow-through openings into a support ring and ultimately escapes outward into the coolant channel via exhaust openings.

A disadvantage in such embodiments that require a transition of the coolant air between the rotating part and the stationary part of a computed tomography apparatus is that unwanted high pressure fluctuations (and consequently noise stress for patient and operator) occur given flowing coolant air and simultaneous rotation.

SUMMARY OF THE INVENTION

The present invention is to provide a gantry for a computed tomography apparatus wherein the noise stress in the operation of the gantry is reduced. A further object of the present invention is to provide a computed tomography apparatus having such a gantry, as well as a method for cooling such a gantry.

The above object is achieved in accordance with the invention by a gantry for a computed tomography apparatus having a rotary carriage that can rotate around an axis and a support ring arranged around the rotary carriage with a circumferential cooling channel, wherein the support ring has a number of openings distributed around its circumference and forming a non-uniform opening pattern, through which openings in operation a coolant between the support ring and the rotary carriage flows into the rotary carriage via openings opposite the openings of the support ring.

An advantage of this embodiment is that the distribution of the pressure fluctuations or the perception of the generated noises upon transition of the coolant from the stationary part to the rotating part of the gantry and vice versa is influenced by the non-uniform opening pattern. In the operation of the computed tomography apparatus a local pressure fluctuation is generated every time when an opening at the rotary carriage overlaps with an opening at the support ring. This local pressure fluctuation causes a noise at a base frequency corresponding to the rotational frequency of the rotary carriage. Given identical intervals between the openings and identical opening geometry a very low-frequency, uncomfortable disruptive noise results. This problem is counteracted in accordance with the invention by the non-uniform opening pattern both at the rotary carriage and at the support ring. An overlap of the openings with non-uniform time intervals and duration as it is achieved by the present invention allows a steady, uniform increase and decrease of the quantity of coolant flowing through, and thus of the pressure in the different parts of the gantry. Abrupt pressure fluctuations are avoided due to the non-uniform opening pattern. This leads to a "smeared" noise which is not as uncomfortable to the human ear as a noise with a high tonal proportion, thus a noise in which individual frequencies are particularly strongly pronounced.

A further advantage that likewise results due to the non-uniform opening pattern is the reduced number of overlapping openings and thus a reduced amplitude of the pressure fluctuation in the gantry. Given similarly arranged uniform openings, as is conventional, upon rotation a number of openings of the rotary carriage simultaneously overlap with openings of the support ring. This leads to a sudden pressure drop which generates a loud disruptive noise. With an opening pattern without predominant regularity and periodicity on at least one of the parts of the gantry, it is ensured that few openings simultaneously overlap, such that the pressure drop does not ensue as abruptly and the disruptive noise is reduced.

At least a portion of the openings on the support ring preferably exhibit different intervals in the circumferential direction relative to their adjacent openings, such that the irregular opening pattern is fashioned in a simple manner.

In a preferred embodiment, in order to produce the irregular opening pattern it is provided that at least two openings on the support ring that are adjacent in the circumferential direction differ with regard to their geometry, different shape and/or size and/or angular bearing of the adjacent openings. The geometry of the openings, in particular on the rotary carriage, is thereby adapted to the cooling requirements. The size of the openings (in particular on the rotary carriage) is thereby adapted to the cooling requirements. The size of the openings depends on the coolant requirement and on the current resistance of the components to be cooled, while not impairing the mechanical stability of the components.

At least some of the openings on the support ring (in particular more than 50% of the openings) are fashioned as a type of oblong hole angled relative to the circumferential direction. This shape of the openings of the support ring has proven to be particularly advantageous. A gradual increase of the area of the overlapping cutouts in the material ensues independent of the shape of the openings on the rotary carriage when two openings on the rotating part and stationary part meet. This is achieved by a steady decrease of the area of the overlapping cutouts. No sudden pressure fluctuations, triggered by fast variations of the coolant flow, occur in the gantry.

The oblong holes preferably exhibit a ratio in the range between 3:1 and 8:1 between their longitudinal axis and their transverse axis.

In a preferred embodiment, a circumferential cooling ring that has a pressure channel that is part of the cooling channel is mounted on a circumferential side of the support ring. The cooling channel thus can be divided into two regions. The first region is the pressure channel in which the coolant is located under high pressure. The second region is a suction channel that radially surrounds the circumferential side of the support ring from the outside and is connected in terms of flow with the pressure channel via a cooling space, such that the coolant flowing out from the pressure channel flows into the suction channel. An advantage of this embodiment is that the rotary carriage is arranged in the cooling space, such that coolant flows through the rotary carriage and the components to be cooled are thus efficiently cooled.

In another embodiment the cooling ring is axially, centrally positioned within the support ring and flanked on both sides by cooling spaces. The coolant that flows out from the pressure channel is thereby uniformly distributed around the cooling ring and provides for an effective coolant distribution and uniform cooling of the components of the rotary carriage on both sides of the cooling ring.

The openings on the cooling ring can form two circles arranged essentially concentric to the axis.

The pressure channel is preferably provided with pressure openings that exhibit a maximum size of approximately 5,000 mm$^2$.

The circumferential side of the support ring is furthermore preferably provided with suction openings that exhibit a maximum size of approximately 10,000 mm$^2$.

The rotary carriage can be formed by two separate parts that are supported in the two cooling spaces.

A further feature of the gantry is that, in operation, the openings of the rotary carriage form overlapping opening pairs with the pressure openings and the suction openings for feedthrough of the coolant. These opening pairs are arranged such that maximally five opening pairs (in particular maximally three opening pairs) simultaneously begin or end an overlap. The local pressure fluctuations are kept low by the limitation of the number of the overlapping openings pairs.

The above object is also achieved in accordance with the invention by a computed tomography apparatus with a gantry according to any of the above-described embodiments.

The above object also is achieved, according to the invention by a method for cooling a gantry of a computed tomography apparatus wherein a rotary carriage rotatable around an axis and a support ring arranged around the rotary carriage with a circumferential cooling channel, including the steps of causing a coolant to flow between the support ring and the rotary carriage at overflow points and steadily increasing and decreasing the quantity of coolant flowing through the overflow points.

DESCRIPTION OF THE DRAWINGS

FIG. 6 is a perspective view of the complete front rotary supporting part of the rotary carriage according to FIG. 4 with internal components.

DESCRIPTION OF THE PREFERRED EMBODIMENTS

Figure 1:
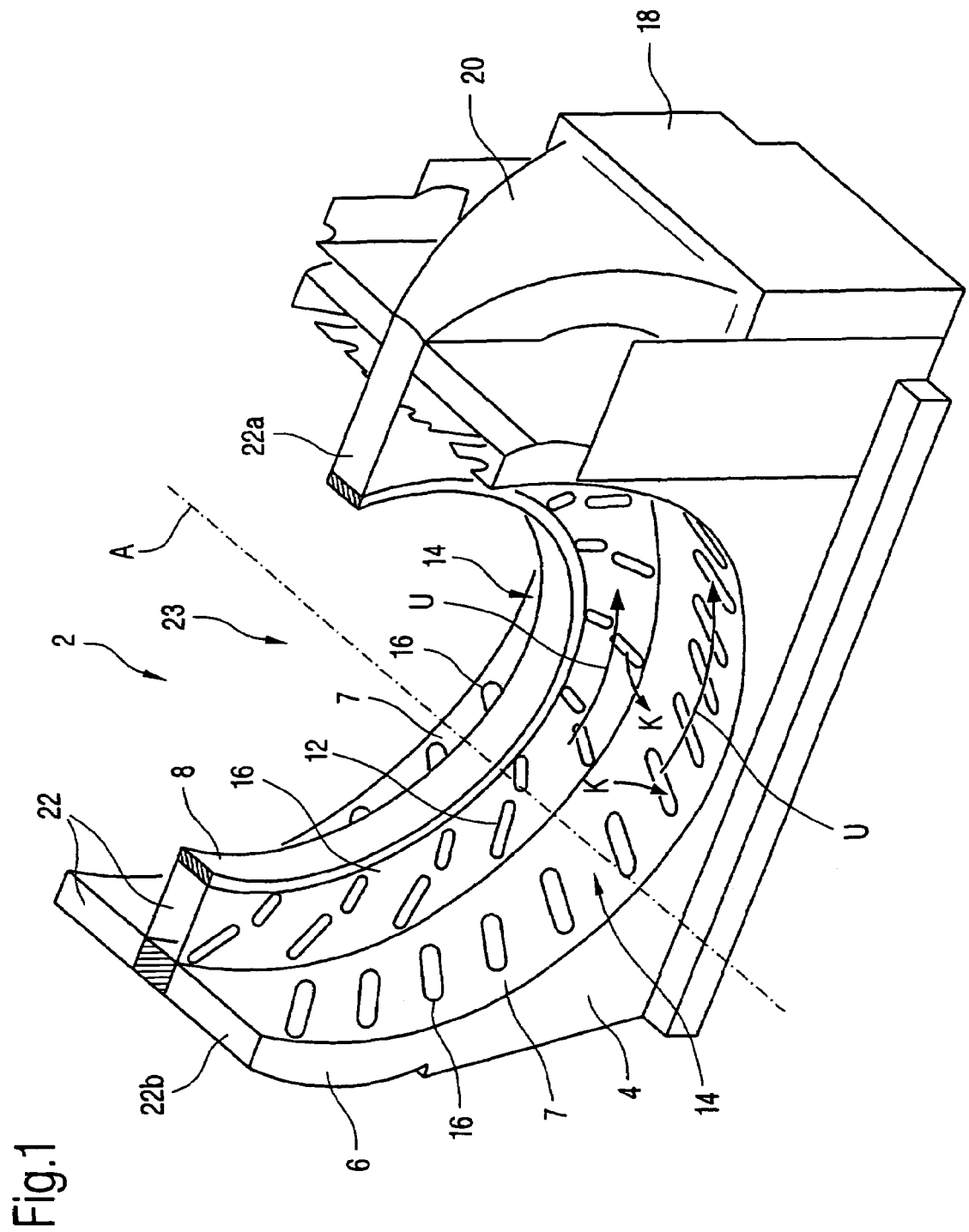
FIG. 1 is a schematic representation of a portion of a computed tomography in accordance with the invention.

FIG. 1 is a perspective view of a part of a computed tomography apparatus 2. The computed tomography apparatus 2 has a supporting body 4 that exhibits a cavity and the lower half of a support ring 6. The supporting body 4 and the support ring 6 are fashioned in one piece and integrated with one another. The support ring 6 is arranged rotationally symmetric around an axis A that indicates its axial direction. The support ring 6 comprises a cooling ring 8 oriented in the radial direction on its radially-inward circumferential side 7. Both flanks 10 of the cooling ring 8 are provided with outlets 12 that form two rows in the circumferential direction U. The cooling ring 8 exhibits a smaller axial extent than the support ring 6 and is centrally positioned on the support ring 6 such that two approximately equally large cooling spaces 14 are formed on both sides of the cooling ring. On both sides of the cooling ring 8 each circumferential side 7 exhibits a row of suction openings 16. A cooling module 18 is mounted abutting the supporting body 4, which cooling module 18 is connected via a feed line 20 with a cooling channel 22a in the cooling ring 8. The cooling module 18 and the supporting body 4 are connected with one another in terms of flow and can be viewed as a whole. The support ring 6 is essentially hollow and has a suction channel 22b, such that the coolant K flows out from the cooling spaces 14 via the suction openings 16 and into the suction channel 22b. The pressure channel 22a and the suction channel 22b are in fluid communication with one another via the cooling spaces 14 and can be considered as two parts of a cooling channel 22.

Figure 4:
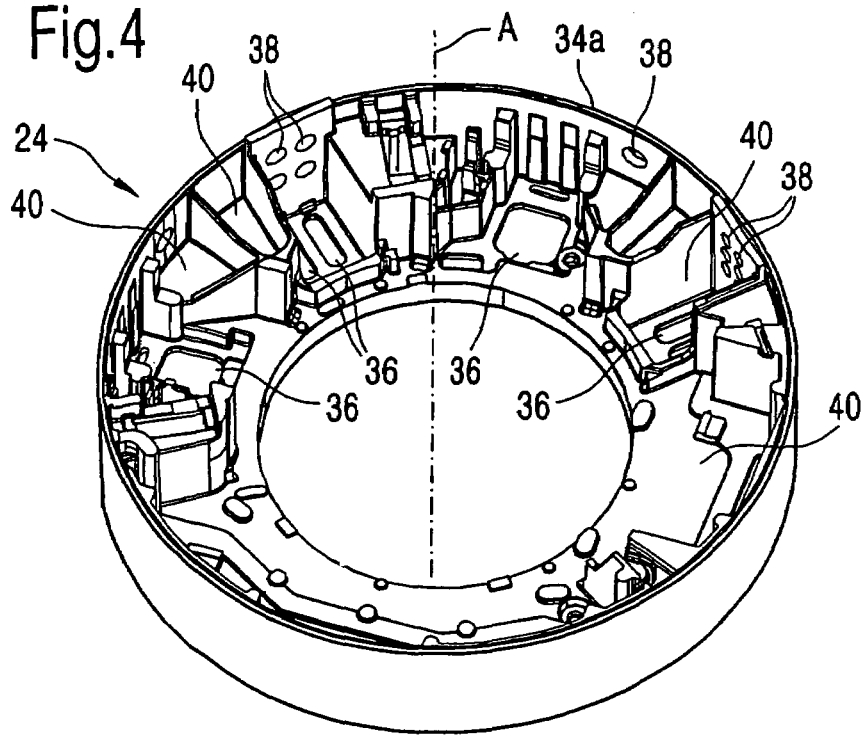
FIG. 4 is a perspective view of a front rotary supporting part of the rotary carriage.
Figure 5:
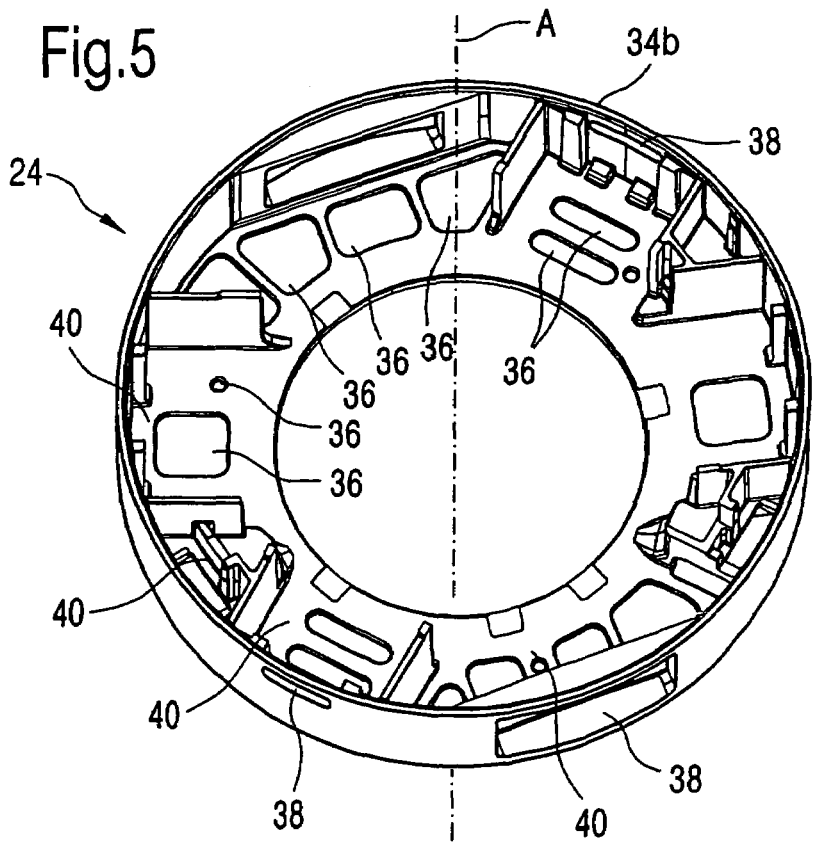
FIG. 5 is a perspective view of a rear rotary supporting part of the rotary carriage.

In order to complete the gantry 23 of the computed tomography apparatus, a rotatable rotary carriage 24 that has at least one x-ray radiator 26 and one diametrically opposite x-ray detector 28 is mounted around the support ring 6 (see FIGS. 4, 5 and 6). The rotary carriage 24 thereby fills the cooling spaces. 18. The annular design of the cooling spaces 18 and the rotary carriage 24 enables the x-ray radiator 26 and the x-ray detector 28 to rotate as well given rotation of the rotary carriage 24 without hindering its rotation movement capability.

For achieving an efficient cooling system for cooling of the gantry 23 a coolant K (in this embodiment air) is fed from the cooling module 18 into the cooling channel 22a of the cooling ring 8 via the feed line 20. The coolant K flows axially out from the cooling channel 22a via the pressure outlets 12 into the rotary carriage 24 in which the components 26, 28 to be cooled are located. The coolant K flows around or through the components heated in the operation of the x-ray radiator 26. The heated coolant K flows radially out from the rotary carriage 24 through the suction openings 16 and arrives in the suction channel 22b. The suction channel 22b is in fluid communication with the cooling module 18 and the coolant K is suctioned by a ventilator (not shown here) located in the cooling module 18 and re-supplied to the pressure channel 22a via the feed line 20. A coolant circuit is formed in the computed tomography apparatus 2 in this manner. In the exemplary embodiment shown in the figures the coolant circuit is closed. A heat exchanger is provided for dissipation of the heat from the coolant. However, the coolant circuit can also be open. Given an open circuit further openings are provided via which the environment air is continuously or discontinuously supplied and also via which a portion of the coolant K in the circuit is discharged.

Figure 2:
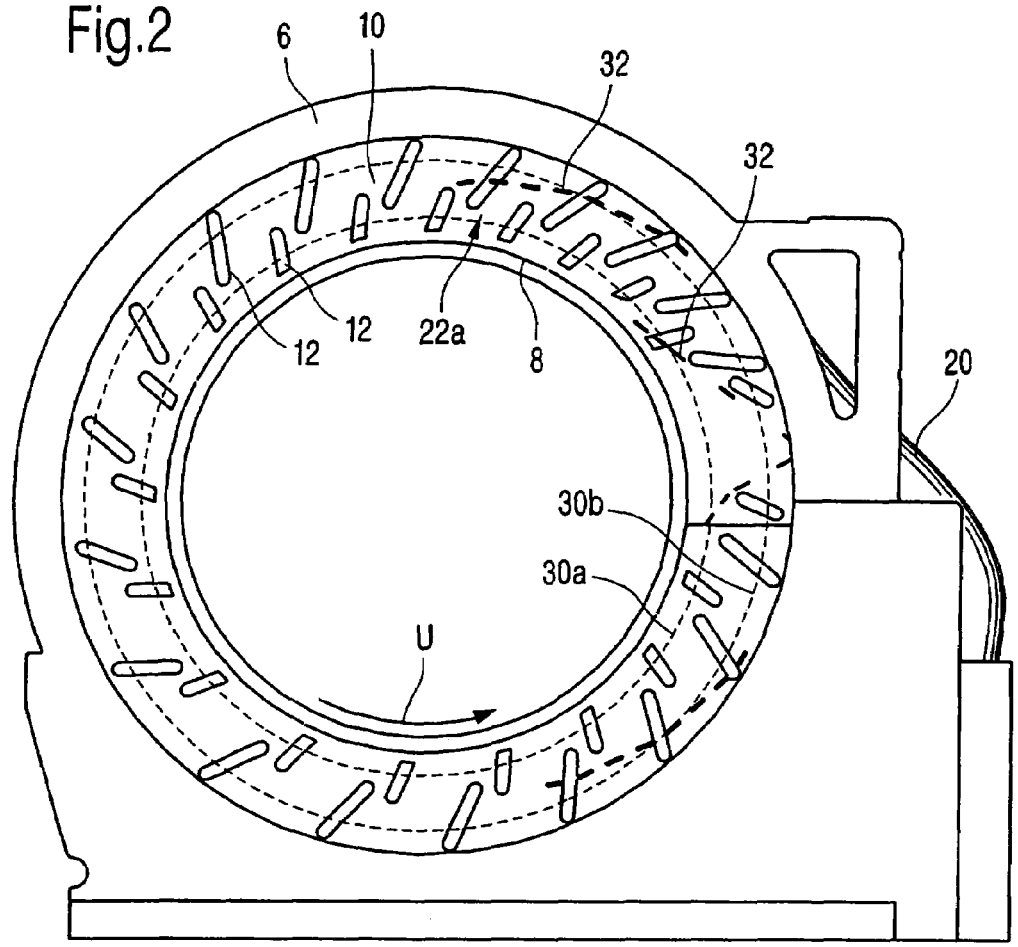
FIG. 2 is a front view of a section in the radial direction through the support ring of the computed tomography apparatus of FIG. 1.

The positioning and alignment of the pressure openings 12 is shown in a section through the support ring 6 in the radial direction in FIG. 2. The flank 10 of the pressure channel 22a or, respectively, of the cooling ring 8 is provided with a number of pressure openings 12 that are arranged in two approximately concentric circles 30a, 30b over the entire circumference of the flank 10.

The pressure openings 12 essentially exhibit the shape of an oblong hole, meaning that they exhibit two edges running parallel to one another. Other shapes (such as, for example, an elliptical design of the pressure openings 12) are also possible. The pressure openings 12 are fashioned angled relative to the circumferential direction U so that the quantity of coolant K flowing out gradually rises and falls given a beginning congruence of a pressure opening 12 with an opening on the rotary carriage 24. The longitudinal direction of the pressure openings 12 is therefore oriented at an angle relative to the radial direction, thus relative to an axis running through the center point of the support ring 6. In the exemplary embodiment this angle is constant; however it can also vary over the circumference. The pressure openings 12 moreover exhibit different sizes. The pressure openings 12 of the (radially) outer circle 30b are in principle larger than the pressure openings 12 of the inner circle 30a. The larger pressure openings exhibit a size of approximately 5,000 mm$^2$ and a ratio in the range between 8:1 and 4:1 between their longitudinal axis and their transverse axis. The smaller pressure openings 12 exhibit smaller ratios which lie in the range between 3:1 and 5:1 between their longitudinal axis and their transverse axis. At least some of the intervals between adjacent pressure openings 12 of a circle 30a, 30b are different.

The cross-section of the pressure channel 22a varies in the circumferential direction. A maximum cross-section is positioned in the range in which the feed line 20 discharges. Positioned diametrically opposite this is a minimum cross-section, whereby the cross-section of the pressure channel 22a steadily decreases from the maximum cross-section in the direction of the minimum cross-section. An essentially constant flow speed is set in the pressure channel 22a via these measures. Due to the varying cross-section of the pressure channel 22a the pressure openings 12 in the region of the minimal cross-section are fashioned smaller than the pressure openings of the same circle 30a, 30b in the region of the feed line 20.

Moreover, baffles 32 that enable a better distribution of the coolant K (by directing the flow thereof) are mounted inside the pressure channel 22a.

Upon inflow of compressed coolant K into the cooling channel 22a in the region around the feed line 20, the flow splits in two directions (abetted by the baffles 32) and flows over the two semi-circular arcs of the cooling ring 8 in the direction of the minimum cross-section 34.

Figure 3:
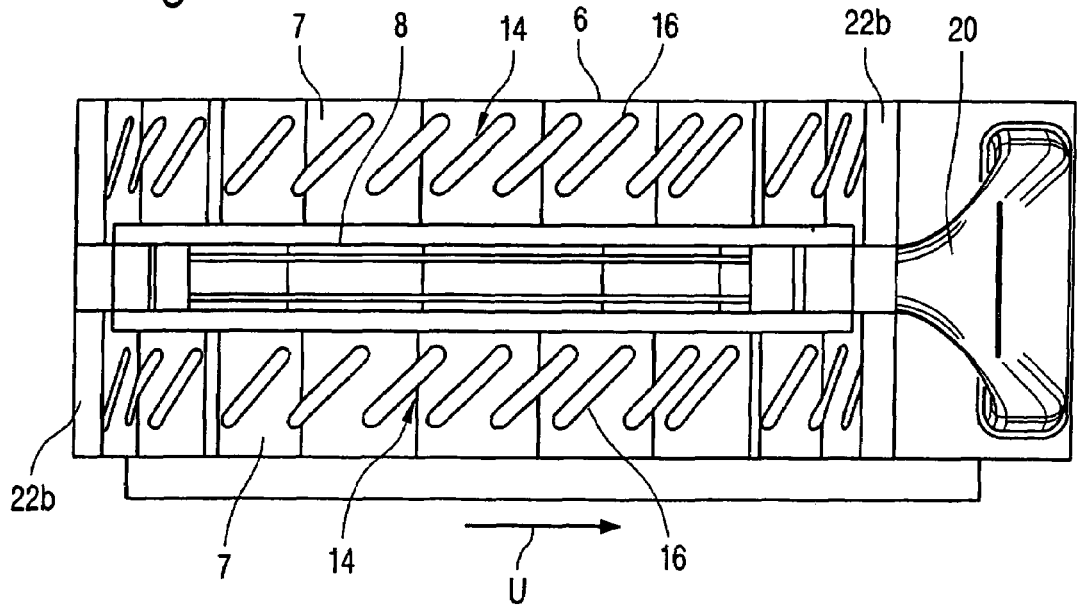
FIG. 3 is a plan view of the lower half of the support ring according to FIG. 2.

After the coolant K has cooled the components 26, 28 to be cooled in the rotary carriage 24, the coolant K (heated in the meanwhile) arrives in the suction channel 22b of the support ring 6 via the suction openings 16. FIG. 3 represents a plan view of the lower half of the support ring 6 from which the geometry of the suction openings 16 is to be learned. The circumferential side 7 of the support ring 6 is divided by the cooling ring 8 into two approximately equal parts and suction openings 16 are arranged in a row on each of these parts. Like the pressure openings 12, the suction openings 16 are fashioned as a type of oblong hole slanted relative to the circumference direction U, and their maximum size is approximately 10,000 mm$^2$. However, as with the pressure openings 12 other shapes are also conceivable. The suction openings 16 moreover exhibit different distances to their neighbors. The suction channel 22b is located under the circumferential side.

In operation the rotating rotary carriage 24 is arranged in the cooling spaces 14. The outer circumferential sides of the rotary carriage 24 are hereby arranged at a slight radial separation relative to the circumferential side 7 divided into two parts. Only a small air gap is present between the rotary carriage 24 and the circumferential side 7. After the components 26, 28 located in the rotary carriage 24 are cooled, the coolant K is sucked into the suction channel 22b via the suction openings 16. The coolant K there is cooled in the hollow supporting body 4 and finally supplied to the cooling ring 8 via the feed line 20.

FIG. 4 and FIG. 5 illustrate the design of a rotary supporting part 34a, 34b of the rotary carriage 24. The rotary supporting part 34a, 34b is fashioned in two parts: the front rotary supporting part 34a (relative to the orientation of the computed tomography apparatus in FIG. 1) is shown in FIG. 4 and the rear rotary supporting part 34b is shown in FIG. 5. Both rotary supporting parts 34a, 34b exhibit inflow openings 36 of different shape, size and orientation on their circumferential sides radially oriented transverse to the axis A, via which inflow openings 36 the coolant K flows into the rotary carriage 24. Outflow openings 38 for the outflow of the heated coolant after the cooling of the components 26, 28 to be cooled are arranged in the axial circumferential sides oriented parallel to the axis A. Like the inflow openings 36, the outflow openings 38 exhibit different shape, size and position. The geometry of the openings 36, 38 is in both cases adapted to the shape, size and position of the components 26, 28 to be cooled as well as the coolant requirement. The rotary supporting parts 34a, 34b internally comprise separated partitions 40 for bearing of the components 26, 28.

The complete front rotary supporting part 34a of the rotary carriage 24 with internals is shown in FIG. 6. Two x-ray radiators 26, two oppositely-situated x-ray detectors 28 (that are respectively covered with a cover 42 to form a closed air chamber) and further associated electronic units 44 are arranged in the rotary supporting part 34a.

Upon rotation of the rotary carriage 24 the inflow openings 36 cover the pressure openings 12 of the cooling ring 8 and thus form opening pairs, such that coolant is injected into rotary carriage via the openings pairs. Due to the shape and the canted alignment of the pressure openings 12 the passed quantity of coolant K steadily increases and decreases and thus the pressure also only oscillates steadily, such that a sudden pressure drop is avoided.

The coolant flows around and through the components 26, 28, 40 in order to transport their heat away. Upon overlap of the outflow openings 38 with the suction openings 16 in the operation of the rotary carriage 24, the heated coolant then flows into the suction channel 22 via the opening pairs hereby formed. A steady variation of the coolant quantity as well as of the pressure in the rotary carriage 24 also ensues here due to the slanted, oblong design of the suction openings 16.

The irregular opening pattern on the cooling ring 8, on the rotary supporting parts 30a, 30b and on the circumferential side 7 of the support ring 6, i.e. the irregular intervals between adjacent openings 12, 16, 36, 38 and the different shape, size and angular position of the openings 12, 16, 36, 38, moreover leads to the situation that only a few opening pairs are simultaneously formed. In particular no more than three opening pairs simultaneously begin or end an overlap. An abrupt pressure variation is thus effectively prevented, which results in the reduction of the noise stress in the operation of the computed tomography apparatus 2.

Although modifications and changes may be suggested by those skilled in the art, it is the intention of the inventors to embody within the patent warranted hereon all changes and modifications as reasonably and properly come within the scope of their contribution to the art.

We claim as our invention:

1. A gantry for a computed tomography apparatus comprising:
   a rotary carriage mounted to be rotatable around an axis, said rotary carriage having an outer circumference with a plurality of openings therein;
   a support ring having an inner circumference surrounding said outer circumference of said rotary carriage, in which said rotary carriage rotates around said axis, said support ring containing a circumferential cooling channel in which coolant flows; and
   said support ring having a plurality of openings therein distributed in a non-uniform opening pattern around said inner circumference of said support ring, said openings in said outer circumference of said rotary carriage and said openings in said inner circumference of said support ring coming to positions opposite one another as said rotary carriage rotates around said axis, to allow said coolant to flow from said cooling channel into said rotary carriage.

2. A gantry as claimed in claim 1 wherein at least some of said openings in said inner circumference of said support ring have different spacing intervals around said circumference relative to adjacent openings.

3. A gantry as claimed in claim 1 wherein respective openings in said plurality openings in said inner circumference of said support ring, that are adjacent to each other, differ in opening geometry.

4. A gantry as claimed in claim 1 wherein at least some of said openings in said plurality of openings in said inner circumference of support ring are oblong holes respectively slanted relative to said circumference.

5. A gantry as claimed in claim 4 wherein said oblong holes have a ratio of longitudinal axis to transverse axis in a range between 3:8 and 8:1.

6. A gantry as claimed in claim 1 comprising a circumferential cooling ring mounted at an exterior circumference of said cooling channel, forming a pressure channel as a part of said cooling channel.

7. A gantry as claimed in claim 6 wherein said cooling ring is disposed axially centrally within said support ring and has cooling spaces respectively disposed on opposite sides thereof.

8. A gantry as claimed in claim 6 wherein said cooling ring has openings therein forming two circles substantially concentric to said axis.

9. A gantry as claimed in claim 6 wherein said pressure channel has pressure openings therein having a maximum size of approximately 5,000 $mm^2$.

10. A gantry as claimed in claim 9 wherein said support ring has suction openings therein having a maximum size of approximately 10,000 $mm^2$.

11. A gantry as claimed in claim 7 wherein said rotary carriage comprises two separate parts respectively supported in said cooling spaces.

12. A gantry as claimed in claim 11 wherein said openings in said inner circumference of said rotary carriage form overlapping opening pairs with the pressure openings and the suction openings for passage of said coolant therethrough, said openings in said outer circumference of said rotary carriage being disposed so that a maximum of five of said opening pairs simultaneously begin or end an overlap of each other.

13. A computed tomography apparatus comprising:
   an x-ray source and a radiation detector; and
   a gantry comprising a rotary carriage, on which said x-ray source and said radiation detector are mounted for rotation around an axis, said rotary carriage having an outer circumference with a plurality of openings therein, a support ring having an inner circumference surrounding said outer circumference of said rotary carriage, in which said rotary carriage rotates around said axis, said support ring containing a circumferential cooling channel in which coolant flows, and said support ring having a plurality of openings therein distributed in a non-uniform opening pattern around said inner circumference of said support ring, said openings in said outer circumference of said rotary carriage and said openings in said inner circumference of said support ring coming to positions opposite one another as said rotary carriage rotates around said axis, to allow said coolant to flow from said cooling channel into said rotary carriage.

14. A method for cooling a gantry of a computed tomography apparatus having a rotary carriage that is rotatable around an axis and a support ring disposed around the rotary carriage, and a cooling ring disposed around said support ring and having a circumferential cooling channel therein comprising the steps of:
   causing cooling to flow between said support ring and said rotary carriage at a plurality of flowthrough points;
   by relative arrangement of said flowthrough points during rotation of said rotary carriage, causing a quantity of coolant flowing through said flowthrough points to continually increase and decrease; and
   introducing said coolant into said rotary carriage from said cooling channel via pressure openings in a non-uniform opening pattern in said support ring, and discharging cooling from said rotary carriage via suction openings at a circumferential side of said cooling ring.

15. A method as claimed in claim 14 comprising, during rotation of said rotary carriage, forming opening pairs for passage of said coolant into said rotary carriage by overlapping openings in said rotary carriage with said pressure openings and suction openings, with an overlap beginning or ending simultaneously for a maximum of five of said opening pairs.

* * * * *